(12) United States Patent
Khanuja et al.

(10) Patent No.: US 7,767,798 B2
(45) Date of Patent: Aug. 3, 2010

(54) LOGANIN ANALOGUES AND A PROCESS FOR THE PREPARATION THEREOF

(75) Inventors: Suman Preet Singh Khanuja, Lucknow (IN); Santosh Kumar Srivastava, Lucknow (IN); Ankur Garg, Lucknow (IN); Merajuddin Khan, Lucknow (IN); Mahendra Pandurang Dardokar, Lucknow (IN); Anirban Pal, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 1118 days.

(21) Appl. No.: 11/366,687

(22) Filed: Mar. 2, 2006

(65) Prior Publication Data

US 2007/0123474 A1 May 31, 2007

(30) Foreign Application Priority Data

Nov. 25, 2005 (IN) .......................... 3158/DEL/2005

(51) Int. Cl.
*C07H 15/00* (2006.01)
(52) U.S. Cl. ..................................... 536/18.2; 536/18.5
(58) Field of Classification Search ....................... None
See application file for complete search history.

(56) References Cited

OTHER PUBLICATIONS

Madhusudanan et al., "Characterization of Iridoid by Fast Atom Bombardment Mass Spectrometry Followed by Collision-Induced Dissociation by [M+Li]+ Ions," Journal of Mass Spectrometry, 35(3), 321-329 (2000); see also reference 3 of 43 for Abstract in search notes.*

Vijayavitthal et al., "Modified Iridoid Glycosides. Part 3. Synthesis and Hepatoprotective Evaluation of Modified Iridoid Glycosides," Indian Journal of Chemistry, Section B: Organic Chemistry Including Medicinal Chemistry, 35B(10), 1056-1061 (1996); only abstract supplied in the search notes—see reference 5 of 43.*

Raj et al., "Modified Iridoid Glucosides. (Part-1). Synthesis of 4'-5'-Unsaturated Iridoid Glycosides from Loganin and Arbortristoside-A," Natural Products Letters, 7(1), 51-58 (1995); only abstract supplied in the search notes—see reference 6 of 43.*

\* cited by examiner

*Primary Examiner*—Lawrence E Crane
(74) *Attorney, Agent, or Firm*—John P. White; Cooper & Dunham LLP

(57) ABSTRACT

The present invention provides novel loganin analogues and a process for the preparation thereof. The present invention further provides the use of Iridoid glycoside loganin isolated from the fruit pulp of *Strychnos nux-vomica* and its bioactive semi-synthetic analogues against various human cancer cell lines grown in-vitro.

16 Claims, 1 Drawing Sheet

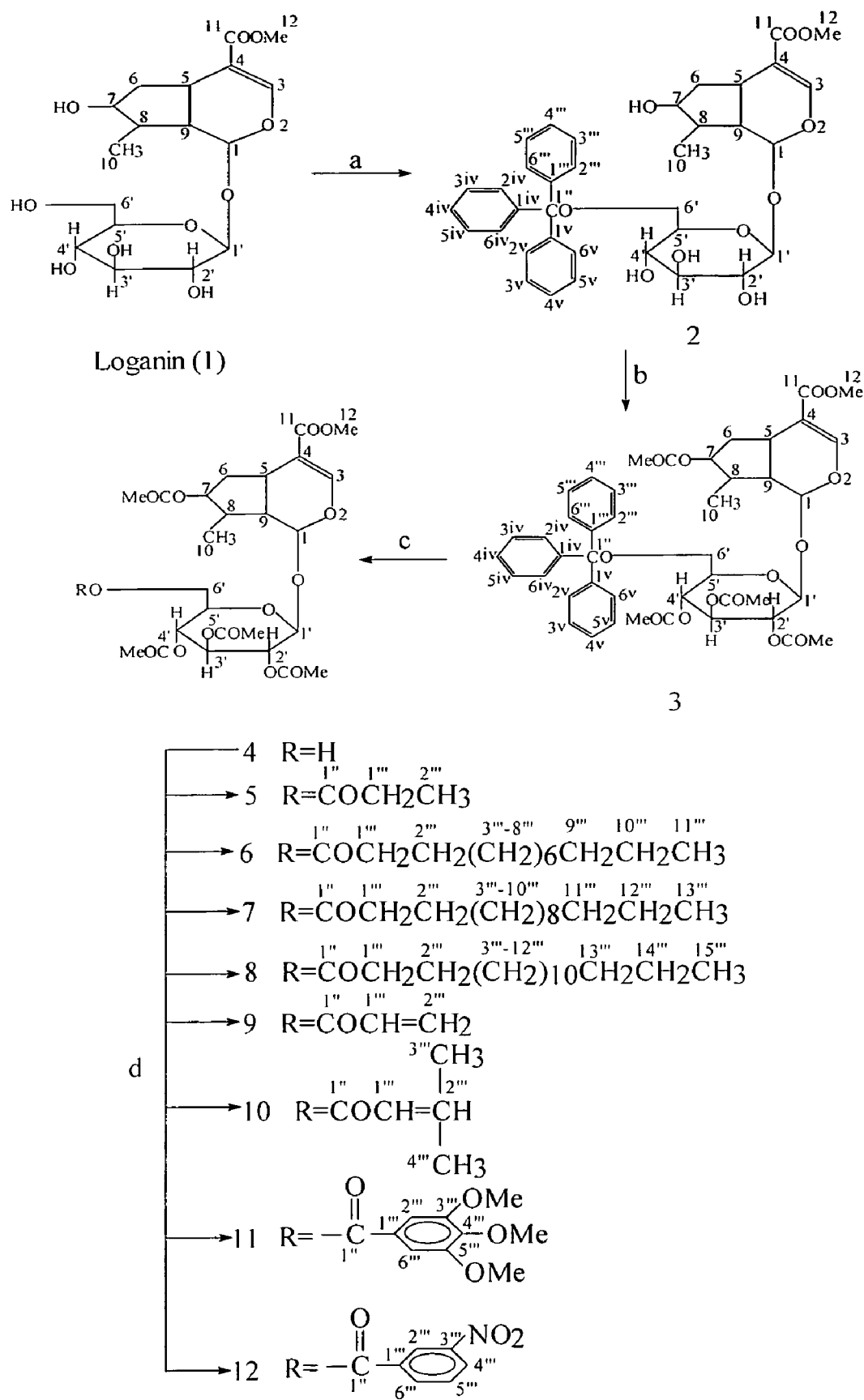

LOGANIN ANALOGUES AND A PROCESS FOR THE PREPARATION THEREOF

This application claims priority of Indian Patent Application No. 3158/DEL/2005, filed Nov. 25, 2005, the contents of which are hereby incorporated by reference into this application.

FIELD OF INVENTION

The present invention relates to novel loganin analogues and a process for the preparation thereof. More particularly the present invention relates to use of Iridoid glycoside loganin isolated from the fruit pulp of *Strychnos nux-vomica* and its bioactive semi-synthetic analogues against various human cancer cell lines grown in-vitro.

BACKGROUND OF INVENTION

Cancer is one of the most dreaded diseases of the 20th century and spreading further with continuance and increasing incidence in 21st century. In the United States, as the leading cause of death, it accounts for 25% of all the deaths in humans presently. It is considered as an adversary of modernization and advanced pattern of socio-cultural life dominated by Western medicine. Multidisciplinary scientific investigations are making best efforts to combat this disease, but the sure-shot, perfect cure is yet to be brought into world of medicine.

Natural anticancer agents are an important area of the current research and are in good demand all over the world. As a result of endless efforts by the scientist around the world, certain lead molecule such as vincristine (VCR), vinblastine (VLB), taxol and camptothecin have been discovered as nature's boon for cancer therapy.

Iridoid glycosides are important natural product and occur in a large number of plant families. Many reviews have dealt with their distribution, structure, properties and biosynthesis (Balachandran, P. Govindarajan, R. *Pharmacological Research.* 2005, 51, 19; El-Naggar, L. J. Beal, J. L. *J. Nat. Prod.* 1980, 43, 649). They have been reported to possess various biological activities such as antitumoral (Ishiguru, K.; Yamaki, M.; Takayi, S.; Ikada, Y.; Kawakani, K.; Ito, K.; Nose, T. *Chem. Pharm. Bull.* 1986, 34, 23) hemodynamic (Circosta, C.; Occhiuto, F.; Ragusa, S.; Trovato, A.; Tumino, G.; Briguglio, F.; De Pasquale, A.; *J. Ethnopharmacol.* 1984, 11, 259.), cholaratic (Miyagoshi, M.; Amagaya, S.; Ogihara, Y.; *J. Pharmabiodyn.* 1988, 11, 186), hepatoprotective (Chang, I. M.; Ryu, J. C.; Park, I. C.; Yun, H. S.; Yang, K. H. *Drug Chem. Toxicol.* 1983, 6, 443), antimicrobial, hypotensive, analgetic, antichloristic, sedative, laxative and various other effects (Sticher, O. (1977) In; *New Natural Products and Plant Drugs with Pharmacological, Biological or Therapeutical Activity,* (Wagner, H.; Wolff, P.; eds.). 137-176, Springer Verlag, Berlin).

Loganin, an iridoid glycoside is the major constituent of *Strychnos nux-vomica* fruit pulp. It has long been used as a precursor for the biosynthesis of indole alkaloids and lately it has been reported to posses various pharmacological activities (Graiku, K.; Aligiannis, N.; Chinou, I. B.; Harvala, C. Z. *Naturforsch.* 2002, 57C, 95; Mathad, V. T.; Raj, K.; Bhaduri, A. P.; Sahai, R.; Puri, A.; Tripathi, L. M.; Srivastava, V. M. L.; *Bioorganic & Meidcinal Chemistry,* 1998, 6, 605; Visen P. K. S.; Saraswat, B.; Raj, K.; Bhaduri, A. P.; Dubay, M. P.; *Phytotherapy Research,* 1998, 12, 405; Raj, K.; Matahad , V. T.; Bhaduri, A. P.; *Ind. J. Chem.,* 1996, 35B, 1056; Recio, M. C.; Griner, R. M.; Manez, S.; Rias, J. L. *Planta Med.,* 1994, 60, 232; Tandon, J. S.; Srivastava, V.; Guru, P. Y. *J. Nat. Prod.* 1991, 54, 1102; Handa S. S.; Sharma, A.; Chakroborti, K. K. *Fitoterapia,* 1986, 27, 307; Woerdengbag H. J.; Moska T. A.; Pras, N,; Malingre T. M. *J. Nat. Prod.* 1993, 56, 849. *Strychnos* Linn. (Fam. Loganiaceae) a large genus of scandent shrub or trees, found throughout the tropic and subtropics. Nearly 20 species occur in India, of which *Strchnos nux-vomica* renowned for the drug value of its poisonous alkaloids, Strychnine and Brucine. *Strchnos nux-vomica* is commonly known as Snake-wood or nux-vomica tree (Anonymous, wealth of India, vol X. CSIR, New Delhi, 1961, 62).

Chemical investigations:

On going through the literature it was observed that loganin, a bitter glycoside isolated from *Strchnos nux-vomica* (Dunstan, W. R.; Short, F. W.; *Pharm J Trans,* 1983, 14, 1025; Merz, K. W.; Kerbs, K. G.; *Arch Pharm,* 1937, 275, 217; Meez, K. W.; Lehmann, H.; *Arch Pharm,* 1957, 290, 543) and other species of strychnos, *Menyanthes trifoliate, Lonicera* and *Hydrangea*-species has recently been the subject of various chemical and biosynthetic investigations. In 1974 Bisset et al isolated loganin from the fruit pulp of *Strchnos nux-vomica* as a major iridoid along with other minor iridoids and alkaloids. In the same year Isiguro et al reported the antitumor activity of several iridoid glycosides and their aglycones. In 1986 Handa et al reported that in traditional system of medicine, an iridoid glycoside (loganin) have a promising protective effect against liver disorders.

In 1991 Tandon et al *J. Nat. Prod.* 1991, 54, 1102, reported the antileishmanial activity of iridoid glycosides both in vitro (against anastigoles in macrophage cultures) and in vivo (in hamsters) test system. In 1994 Ricio et a.l *Planta Med.,* 1994, 60, 232 studied the structrural considerations on the iridoids as anti-infllammatory agents. In 1996 Raj et al. *Ind. J Chem.,* 1996, 35B, 1056, described synthesis of various loganin analogues and their hepatoprotective evaluation with structural activity relationship. In 1998 Mathad et al. *Bioorganic & Meidcinal Chemistry,* 1998, 6, 605 studied the immunostimulant activity profile of modified iridoid glycosides prepared from loganin, keto-loganin and arbortristoside A and some structure activity relationship was carried out.

The detailed literature search revealed that loganin is present in fruit pulp of *Strchnos nux-vomica* in sufficient amount (Bisset, N. G.; Choudhury, A. K. *Phytochemistry,* 1974, 13) and possesses various important biological activities such as hepatoprotective (Raj, K.; Matahad , V. T.; Bhaduri, A. P.; *Ind. J. Chem.,* 1996, 35B, 1056), immunostimulant, antimicrobial and various other effects (Sticher, O. (1977) In; *New Natural Products and Plant Drugs with Pharmacological, Biological or Therapeutical Activity*, (Wagner, H.; Wolff, P.; eds.). 137-176, Springer Verlag, Berlin).

It was also recorded that few short report appeared in literature, refrerence may be made to Bisset, N. G.; Choudhury, A. K. *Phytochemistry,* 1974; Mathad, V. T.; Raj, K.; Bhaduri, A. P.; Sahai, R.; Puri, A.; Tripathi, L. M.; Srivastava, V. M. L.; *Bioorganic & Meidcinal Chemistry,* 1998, 6, 605 and Raj, K.; Matahad , V. T.; Bhaduri, A. P.; *Ind. J. Chem.,* 1996, 35B,1056, on loganin for their various biological activities but to the best of our knowledge no work on the anticancer activity of loganin and its semi-synthetic analogues have been reported so far. Hence we wish to report the anticancer activities of loganin and its new semi-synthetic analogues against various human cancer cell lines grown in-vitro. Isolation of loganin was cariied out from the fruit pulp of *Strychnos nux-vomica*. Further chemical transformation of loganin was carried out to prepare various new synthetic analogues. Finally loganin and its various new synthetic analogues were evaluated for their anticancer activity against various human cancer cell lines.

SUMMARY OF THE INVENTION

Accordingly the present invention provides novel loganin analogues of formula I

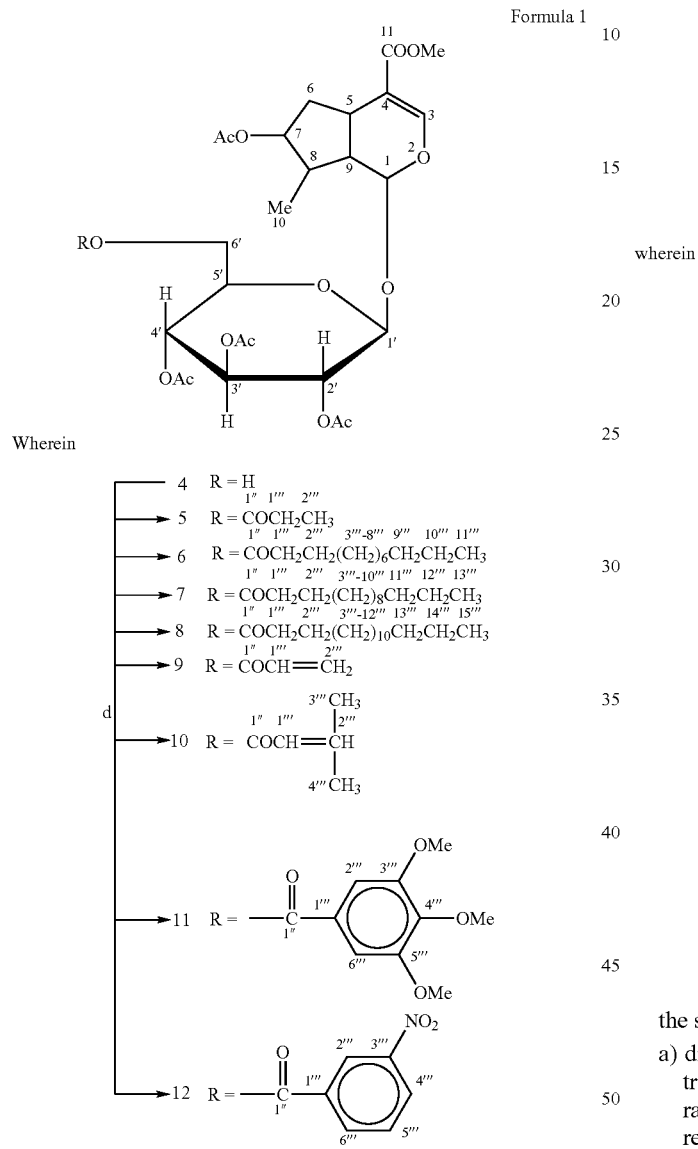

In an embodiment of the present invention the novel loganin analogues of formula 1, are represented by the group of the following compounds:

2',3',4',7-Tetra-O-acetylloganin (4), 2',3',4',7-Tetra-O-acetyl-6'-O-propionylloganin (5), 2',3',4',7-Tetra-O-acetyl-6'-O-lauroylloganin (6), 2',3',4',7-Tetra-O-acetyl-6'-O-myristoylloganin (7), 2',3',4',7-Tetra-O-acetyl-6'-O-palmitoyl loganin (8), 2',3',4',7-Tetra-O-acetyl-6'-O-acryloyl loganin (9), 2',3',4',7-Tetra-O-acetyl-6'-O-3'',3''-dimethyl acryloylloganin (10), 2',3',4',7-Tetra-O-acetyl-6'-O-3,4,5-trimethoxy benzoyl loganin (11), 2',3',4',7-Tetra-O-acetyl-6'-O-(3''')-nitrobenzoyl loganin (12).

The present invention further provides a process for the preparation of loganin analogue of formula 1, the said process comprising the steps of:

a) dissolving loganin (1) in pyridine and reacting it with trityl chloride, under stirring, at a temperature in the range of 30-40° C., adding crushing ice to the above said reaction mixture and extracting the resultant mixture with chloroform and further extracting the resultant extract with about 6% HCl, followed by washing with water and drying by known method to obtain 6'-O-trityl loganin (2), b) acetylating the above said compound (2) in pyridine with acetic anhydride to obtain the compound 2',3',4',7-tetra-O-acetyl-6'-O-trityl loganin (3), c) hydrolyzing the above said compound obtained (3) in step (b) by dissolving it in 70-90% acetic acid solution and refluxing it, at 70-90° C., for about 1 hr, adding water to above said reaction mixture, followed by extraction with chloroform, washing the resultant extract with water till it's neutralization, and drying by known method to obtain the compound 2',3',4',7-tetra-O-acetyl loganin (4), d) acetylating or arylating the above said compound 2',3', 4',7-tetra-O-acetyl loganin (4) obtained in step (c) by dissolving it either chloroform along with catalytic amount of 4-dimethyl amino pyridine (DMAP) or in pyridine and reacting it with desired acid chloride or acid anhydride, for an over night period, at a temperature of 30-45° C., adding ice to the above said reaction mixture and extracting the resultant mixture with chloroform, followed by washing with water till it's neutralization, followed by purification and drying by known method to obtain the desired product from compounds (5) to (12).

In yet another embodiment the trityl chloride used in step (a) is in the range of 1-1.5 equivalent to loganin (1).

In yet another embodiment the compounds (5) to (12) obtained are represented by a group of the following compounds:

6'-O-trityl loganin (2), 2',3',4',7-tetra-O-acetyl-6'-O-trityl loganin (3), 2',3',4',7-tetra-O-acetyl loganin (4), 2',3',4',7-Tetra-O-acetyl-6'-O-propionylloganin (5), 2',3',4',7-Tetra-O-acetyl-6'-O-lauroylloganin (6), 2',3',4',7-Tetra-O-acetyl-6'-O-myristoyl loganin (7), 2',3',4',7-Tetra-O-acetyl-6'-O-palmitoyl loganin (8), 2',3',4',7-Tetra-O-acetyl-6'-O-acryloyl loganin (9), 2',3',4',7-Tetra-O-acetyl-6'-O-3",3"'-dimethyl acryloylloganin (10), 2',3',4',7-Tetra-O-acetyl-6'-O-3,4,5-trimethoxy benzoyl loganin (11), 2',3',4',7-Tetra-O-acetyl-6'-O-(3''')-nitrobenzoyl loganin (12).

The present invention further provides a pharmaceutical composition comprising loganin (1) or its analogues, salts or mixture thereof, optionally with pharmaceutically acceptable carrier, adjuvant and additives.

A composition as claimed in claim 6, wherein the loganin analogues used are represented by a group of the following compounds:

6'-O-trityl loganin (2), 2',3',4',7-tetra-O-acetyl-6'-O-trityl loganin (3), 2',3',4',7-tetra-O-acetyl loganin (4), 2',3',4',7-Tetra-O-acetyl-6'-O-propionylloganin (5), 2',3',4',7-Tetra-O-acetyl-6'-O-lauroylloganin (6), 2',3',4',7-Tetra-O-acetyl-6'-O-myristoyl loganin (7), 2',3',4',7-Tetra-O-acetyl-6'-O-palmitoyl loganin (8), 2',3',4',7-Tetra-O-acetyl-6'-O-acryloyl loganin (9), 2',3',4',7-Tetra-O-acetyl-6'-O-3",3"-dimethyl acryloylloganin (10), 2',3',4',7-Tetra-O-acetyl-6'-O-3,4,5-trimethoxy benzoyl loganin (11), 2',3',4',7-Tetra-O-acetyl-6'-O-(3''')-nitrobenzoyl loganin (12).

In yet another embodiment the loganin used is isolated from the fruits pulp of *Strychnos nux-vomica*.

In yet another embodiment the loganin and its analogues exhibits anticancer activity against human cancer cell.

In yet another embodiment the composition exhibits anti cancer activity against but not limited to breast (MCF-7), Ovary (PA-1), Liver (WRL), Colon (COLO-320, CaCo2) cancer cells.

In yet another embodiment the pharmaceutical composition is useful as cancer chemotherapy agent.

In yet another embodiment the concentration of loganin (1) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 1 to 5 µg/ml.

In yet another embodiment the concentration of 6'-O-trityl loganin (2) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.25 to 2.0 µg/ml.

In yet another embodiment the concentration of 2',3',4',7-tetra-O-acetyl-6'-O-trityl loganin (3) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.80 to 3.50 µg/ml.

In yet another embodiment the concentration of 4',7-Tetra-O-acetyl-6'-O-propionylloganin (5) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.80-3.0 µg/m.

In yet another embodiment the concentration of 2',3',2',3',4',7-Tetra-O-acetyl-6'-O-lauroylloganin (6) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.04 to 0.85 µg/ml.

In yet another embodiment the concentration of 2',3',4',7-Tetra-O-acetyl-6'-O-myristoyl loganin (7) used in vitro MTT assay for IC 50 in cancer cell line MCF-7 of breast cancer, PA-1 of ovary cancer, WRL of liver cancer and COLO-320 of colon cancer is in the range of 6.5 to 59.0 µg/ml.

In yet another embodiment the concentration of 2',3',4',7-Tetra-O-acetyl-6'-O-3",3"-dimethyl acryloylloganin (10) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.08 to 1.20 µg/ml.

In yet another embodiment the concentration of 2',3',4',7-Tetra-O-acetyl-6'-O-3,4,5-trimethoxy benzoyl loganin (11) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.04 to 0.54 µg/ml.

In yet another embodiment the concentration of 2',3',4',7-Tetra-O-acetyl-6'-O-(3''')-nitrobenzoyl loganin (12) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.44 to 3.20 µg/ml.

The present further provides the use of loganin (1) and it's analogues as anticancer activity against human cancer cell lines.

In yet another embodiment the said compounds are active against but not limited to breast (MCF-7), Ovary (PA-1), Liver (WRL), Colon (COLO-320, CaCo2) cancer cells.

In yet another embodiment the dose of loganin (1) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 1 to 5 µg/ml.

In yet another embodiment the dose of 6'-O-trityl loganin (2) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.25 to 2.0 µg/ml.

In yet another embodiment the dose of 2',3',4',7-tetra-O-acetyl-6'-O-trityl loganin (3) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.80 to 3.50 µg/ml.

In yet another embodiment the dose of 4',7-Tetra-O-acetyl-6'-O-propionylloganin (5) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.80-3.0 µg/m.

In yet another embodiment the dose of 2',3',2',3',4',7-Tetra-O-acetyl-6'-O-lauroylloganin (6) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.04 to 0.85 µg/ml.

In yet another embodiment the dose of 2',3',4',7-Tetra-O-acetyl-6'-O-myristoyl loganin (7) used in vitro MTT assay for IC 50 in cancer cell line MCF-7 of breast cancer, PA-1 of ovary cancer, WRL of liver cancer and COLO-320 of colon cancer is in the range of 6.5 to 59.0 µg/ml.

In yet another embodiment the dose of 2',3',4',7-Tetra-O-acetyl-6'-O-3",3"-dimethyl acryloylloganin (10) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.08 to 1.20 µg/ml.

In yet another embodiment the dose of 2',3',4',7-Tetra-O-acetyl-6'-O-3,4,5-trimethoxy benzoyl loganin (11) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.04 to 0.54 µg/ml.

In still another embodiment the dose of 2',3',4',7-Tetra-O-acetyl-6'-O-(3'")-nitrobenzoyl loganin (12) used in vitro MTT assay for IC 50 in cancer cell line MCF-7 of breast cancer, PA-1 of ovary cancer, WRL of liver cancer, COLO-320 of colon cancer and CaCo-2 of Adherent colon cancer is in the range of 0.44 to 3.20 µg/ml.

BRIEF DESCRIPTION OF THE DRAWING

The FIGURE depicts the process for preparing loganin analogues of formula 1.

DETAILED DESCRIPTION OF INVENTION

As part of our studies we first isolated loganin from the fruits pulp of *S. nux-vomica*, and then various new synthetic analogues were prepared. Finally all the analogs along with loganin were tested for their anticancer properties against the five human cancer cell lines in-vitro. The anticancer activity testing was done by MTT assay and finally the results were confirmed by clonogenic assay from which the inhibitory concentration $IC_{50}$ the concentration (ug/ml) of the biomolecules required for 50% inhibition of cell growth was deduced. The data obtained in these bioassays against human cancer cells indicated that the parent molecule loganin showed significant cytotoxic activity against all the tested human cancer cell lines. The new analogous 2',3',4',7-tetra-O-acetyl-6'-O-3,4,5-trimethoxy benzoyl loganin and 2',3',4',7-tetra-O-acetyl-6'-O-lauroyl loganin showed 8-13 times higher activity than the known anticancer drug, vinblastine against the human suspension colon (Colo-320) and human adherent colon (CaCo2) cancer cell lines. While the remaining analogues along with the parent molecule, loganin showed compatible activity with vinblastine against the five tested human cancer cell lines.

The following examples are given by the awy of illustration and therefore should not be construed to limit the scope of the invention.

EXAMPLE-1

Collection of Plant Material and Extraction

The *Strchnos nux-vomica* fruits were collected locally from Lucknow, in the month of December 2000. The pulp of *Strchnos nux-vomica* fruits was obtained by removing seeds and peel from the fruits (~12 Kg), this was successively extracted thrice at room temperature over night with MeOH in a percolator. The combined MeOH extract was concentrated under vacuum on a Buchi rotar vapour and finally dried on a high vacuum pump until the MeOH was completely removed.

The dried methanolic extract was dissolved in distilled water and filtered. The aqueous extract (filtrate) so obtained was fractionated successfully with n-hexane, ethyl acetate and n-butanol saturated with water to yield corresponding extracts.

EXAMPLE-2

Isolation of Loganin from Fruit Pulp of *Strchnos nux-vomica*

All the above fractions (n-hexane, ethyl acetate and n-butanol) were monitored on TLC, which showed that loganin was present in n-BuOH extract. The concentrated n-BuOH extract was kept in refrigerator for overnight, which afforded a white precipitate. The TLC profile of the precipitate showed that it is mainly loganin associated with some minor non polar impurities. Further purification of loganin was carried out as given below in the flow chart.

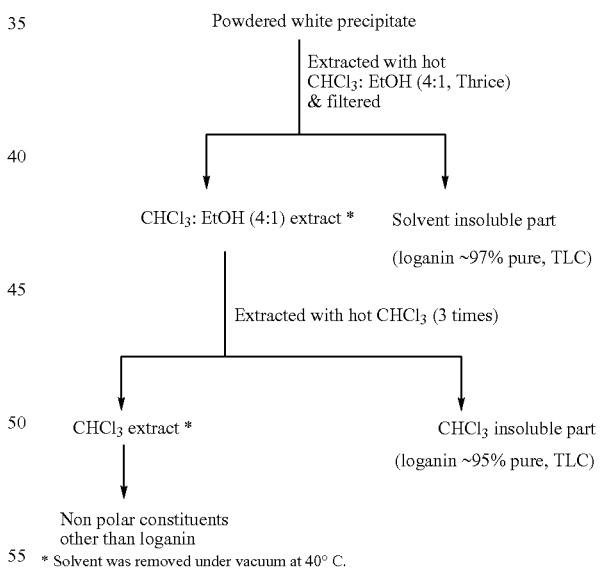

EXAMPLE-3

Preparation of Various Synthetic Analogues of Loganin

Tritylation of Loganin

The loganin was dissolved in pyridine and trityl chloride was added in 1.5 equivalents and stirred at 45° C. for 36 hrs to give the compound 6'-O-trityl loganin (2) in 65% yield.

Work Up of the Reaction

After completion of the reaction, crushed ice was added to the reaction mixture and the mixture was then extracted with chloroform (4 times). The $CHCl_3$ extract was then extracted with 6% HCl solution (4 times). The chloroform solution was then washed with $H_2O$ (until it was neutralized), dried over anhydrous $Na_2SO_4$ and solvent removed under vacuum at 40° C. The TLC profile of $CHCl_3$ extract showed tritylated product as the major component along with several other minor products, which was further purified by column chromatography.

Column Chromatographic Separation of the Tritylated Product

Column chromatographic separation of the tritylated product resulted in isolation of compound, 6'-O-trityl loganin (2) in 65% yield eluted with solvents $CHCl_3$:MeOH (97:3).

Acetylation of Compound 2

Compound 2 was acylated in pyridine with acetic anhydride to give 2',3',4',7-tetra-O-acetyl-6'-O-trityl loganin (3) in 92.1% yield.

Hydrolysis of Compound 3

Compound 3 was dissolved in 80% acetic acid solution and reflux at 80° C. for 1 h. Completion of the reaction was checked by TLC. After completion of the reaction, water was added and extracted four times with chloroform. The pooled chloroform extract was washed with water (until it was neutralized). The neutralized chloroform extract was dried over anhydrous $Na_2SO_4$ and solvent removed under vacuum.

Column Chromatographic Separation of the Hydrolyzed Product

Column chromatographic separation of the hydrolyzed product resulted in the isolation of purified compound, 2',3',4',7-tetra-O-acetyl loganin (4) in 76.7% yield eluted with the solvent system $CHCl_3$: MeOH (99:1).

Preparation of New Acyl/Aryl Analogues of Compound 4

Further partially protected compound 4 was acylated/arylated with different acid chlorides/acid anhydrides by using the following methods.

General Procedure

Method 1:

The partially protected compound, 4 was dissolved in $CHCl_3$ along with catalytic amount of 4-dimethyl amino pyridine (DMAP) and then different acid chlorides/acid anhydrides were added in 1:1.5 ratio. The reaction mixtures were kept overnight at room temperature (30-45° C.). The progress of the reactions was checked by TLC. After completion of the reaction, ice water was added (~15 ml) and reaction solutions were extracted three times with chloroform. The combined chloroform extracts was washed with water (until it was neutralized). The neutralized chloroform extract was dried over $Na_2SO_4$ and concentrated on a rotatory evaporator under reduced pressure.

Method 2:

The partially protected compound, 4 was dissolved in pyridine and then different acid chlorides/acid anhydrides were added in 1:1.5 ratio. The reaction mixtures were kept overnight at room temperature (30-45° C.). The progress of the reaction was checked by TLC. After completion of the reaction, ice cold water was added and the reaction mixture was extracted four times with chloroform. The chloroform extracts were pooled together and washed four times with 6% HCl solution. The chloroform solution so obtained washed with water until it was neutralized. The neutral chloroform extract was dried over anhydrous $Na_2SO_4$ and solvent removed under vacuum at 40° C.

Preparation of Propionyl Derivative of Compound 4 with Propionic Anhydride

The partially protected compound, 4 (200 mg) was dissolved in $CHCl_3$ along with catalytic amount of 4-dimethyl amino pyridine (DMAP) and then propionic anhydride (0.08ml) was added in 1:1.5 ratio. The reaction mixtures were kept overnight at room temperature (32° C.). The progress of the reaction was checked by TLC. After completion of the reaction, ice water was added (~15 ml) and reaction solutions were extracted three times with chloroform. The combined chloroform extracts was washed with water (until it was neutralized). The neutralized chloroform extract was dried over $Na_2SO_4$ and concentrated on a rotatory evaporator under reduced pressure.

Column Chromatographic Separation of Various Acyl/Aryl Derivatives of Compound 4

After work up of the reactions, chloroform extracts of the above acyl/aryl analogues of compound 4 were purified by column chromatographic separation over silica gel using the solvents, hexane and chloroform as eluants in various proportions, which resulted in the isolation of purified products (5-12).

EXAMPLE-4

Identification of Loganin and its Synthetic Analogues

Loganin(1) and its synthetic analogues (5-12) were identified on the basis of their $^1H$ and $^{13}C$ NMR spectroscopic data. $^1H$ and $^{13}C$ NMR spectroscopic data of some selected compounds are given below:

Compound 2: Yield: 65%, m.p.=120° C., $^1$HNMR ($CDCl_3$): δ 1.10 (3H, d, J=6.4 Hz, H-10), 1.50 (1H, m, H-6a), 1.90 (1H, m, H-8), 2.10 (1H, m, H-9), 2.30 (1H, m, H-6b), 2.50 (1H, m, H-5), 3.20 (1H, t, J=8.0 Hz, H-2'), 3.30- 3.40 (3H, m, H-3', H-4' and H-5'), 3.60 (4H, brs, H-12 and H-6'b), 3.80 (1H, brs, H-6'a), 4.00 (1H, brs, H-7), 4.60 (1H, d, J=7.4 Hz, H-1'), 5.10 (1H, d, J=4.6 Hz, H-1), 7.20-7.40 (16H, s, H-3 & Ar—H of 3 phenyl ring), $^{13}$CNMR ($CDCl_3$) C-1 97.60d, C-3 150.50d, C-4 113.40s, C-5 31.60d, C-6 42.40t, C-7 73.80d, C-8 41.30d, C-9 45.80d, C-10 12.90q, C-11 166.00s, C-12 51.00q, C-1' 99.40d, C-2' 74.40d, C-3' 77.00d, C-4' 71.70d, C-5' 75.40d, C-6' 64.10t, C-1" 87.00s, C-1"', 1$^{iv}$ & 1$^v$ 144.10s, C-2"' & 6", 2$^{iv}$ & 6$^{iv}$ and 2$^v$ & 6$^v$ 128.90d, C-3"' & 5"', 3$^{iv}$ & 5$^{iv}$ and 3$^v$ & 5$^v$ 127.90d, C-4"', 4$^{iv}$ and 4$^v$ 126.80d, FABMS: m/z 632 [M$^+$]; 4: Yield 76.7%, m.p.=148-150° C., $^1$HNMR ($CDCl_3$): 1.00 (3H, d, J=6.5 Hz, H-10), 1.75-1.82 (2H, m, H-6a and H-8), 1.90-2.10 (12H, s, 3H each, 4×$OCOCH_3$), 2.20-2.30 (2H, m, H-9 and H-6b), 3.00 (1H, m, H-5), 3.50 (1H, brs, H-6'b), 3.60 (1H, m, H-6'a), 3.70 (4H, s, H-5' and H-12), 4.80 (1H, d, J=7.9Hz, H-1'), 4.90 (1H, m, H-2'), 5.00 (1H, m, H-7), 5.10 (1H, m, H-1), 5.20 (2H, brs, H-3' and H-4'), 7.3 (1 H, s, H-3), $^{13}$CNMR ($CDCl_3$) C-1 95.80d, C-3 150.00d, C-4 114.00s, C-5 30.90d, C-6 39.50t, C-7 77.40d, C-8 39.50d, C-9 46.90d, C-10 12.90q, C-11 167.50s, C-12 51.30q, C-1' 96.90d, C-2' 71.60d, C-3' 75.20d, C-4' 70.00d, C-5' 76.30d, C-6' 63.40t, C-7-$\underline{C}OCH_3$ (169.40s), C-7-CO$\underline{CH}_3$ (20.40q), C-2'-$\underline{C}OCH_3$ (171.40s), C-2'-CO$\underline{CH}_3$ (21.10q), C-3'-$\underline{C}OCH_3$ (170.60s), C-3'-CO$\underline{CH}_3$ (20.9q), C4'-$\underline{C}OCH_3$ (171.2s), C-4'-CO$\underline{CH}_3$ (21.9q), FABMS: m/z 558 [M$^+$] 5: Yield 98.4%, m.p.=92° C., $^1$HNMR ($CDCl_3$): 1.00 (3H, d, J=6.7 Hz, H-10), 1.11 (3H, t, J=7.5 Hz, H-2"'), 1.84-1.90 (2H, m, H-6a and H-8), 1.94, 2.00, 2.04, 2.10 (3H each, s, 4×$OCOCH_3$), 2.22 (2H, m, H-9 and H-6b), 2.31 (2H, m, H-1'''), 3.00 (1H, m, H-5), 3.69 (3H, s, H-12), 3.70 (1H, m, H-5'b), 4.16 (1H, m, H-6'b), 4.28 (1H, m, H-6'a), 4.90 (1H, d, J=8.1 Hz, H-1'), 5.00 (1H, t, J=9.4 Hz, H-2'), 5.10 (2H, m, H-7' and H-3' and H-4'), 7.30 (1H, s, H-1'). $^{13}$CNMR (CDCl$_3$): C-1 95.20d, C-3 149.30d, C-4 113.70s, C-5 30.30d, C-6 39.10t, C-7 77.00d, C-8 39.10d, C-9 46.00d, C-10 12.50q, C-11 168.90s, C-12 51.00q, C-1' 96.30d, C-2' 71.10d, C-3' 72.60d, C-4' 68.60d, C-5' 72.80d, C-6' 62.10t, C-7-$\underline{C}$OCH$_3$ (169.80s), C-7-CO$\underline{CH}_3$ (20.10q), C-2'-$\underline{C}$OCH$_3$ (173.0s), C-2'-CO$\underline{CH}_3$ (20.80q), C-3'-$\underline{C}$OCH$_3$ (170.10s), C-3'-CO$\underline{CH}_3$ (20.4q), C-4'-$\underline{C}$OCH$_3$ (171.9s), C-4'-CO$\underline{CH}_3$ (20.5q), FABMS: m/z 614 [M$^+$], Elemental analysis for C$_{28}$H$_{38}$O$_{15}$ Calc; C, 54.7, H, 6.2; Observ., C, 54.0, H, 6.0, 6: Yield: 98.6, m.p.=Oil, $^1$H NMR (CDCl$_3$): 0.87 (3H, brs, H-11'''), 1.00 (3H, brs, H-10)1.25 (16H, brs, H-3'''-H-10'''), 1.50 (2H, m, H-2'''), 1.75-1.90 (2H, m, H-6a and H-8), 1.99-2.06 (12H, s, 4×OCOCH$_3$), 2.09 (2H, m, H-9 and H-6b), 2.20 (2H, m, H-1'''), 3.00 (1H, m, H-5), 3.70 (4H, brs, H-5' and H-12), 4.16 (1H, m, H-6'b), 4.24 (1H, m, H-6'a), 4.80 (1H, brs, H-1'), 4.90 (1H, d, J=7.9 Hz, H-2'), 5.10 (2H, m, H-7 and H-1), 5.20 (2H, brs, H-3' and H-4'), 7.30 (1H, s, H-3), $^{13}$CNMR (CDCl$_3$): C-1 95.00d, C-3 148.90d, C-4 113.40s, C-5 30.50d, C-6 38.70t, C-7 76.60d, C-8 38.70d, C-9 45.80d, C-10 12.10q, C-11 166.80s, C-12 50.50q, C-1' 96.00d, C-2' 71.00d, C-3' 72.30d, C-4' 68.70d, C-5' 72.50d, C-6' 61.80t, C-1'' 172.80s, C-1''' 33.70t, C-2''' 31.50t, C-3'''-C-8''' 29.8-29.3t, C-9''' 24.40d, C-10''' 22.20t, C-11''' 13.40q, C-7-$\underline{C}$OCH$_3$ (168.9s), C-7-CO$\underline{CH}_3$ (19.6q), C-2'-$\underline{C}$OCH$_3$ (170.9s), C-2'-CO$\underline{CH}_3$ (20.7q), C-3'-$\underline{C}$OCH$_3$ (169.5s), C-3'-CO$\underline{CH}_3$ (20.3q), C-4'-$\underline{C}$OCH$_3$ (170.1s), C-4'-CO$\underline{CH}_3$ (20.4q), FABMS: m/z 740 [M$^+$] Elemental analysis C$_{37}$H$_{56}$O$_{15}$ Calc; C, 60.0, H, 7.6; Observ; C, 59.2, H, 7.4; 9: Yield: 81.0%, m.p=68-70° C., $^1$H NMR (CDCl$_3$): 0.99 (3H, d, J=3.5 Hz, H-10), 1.74-1.87 (2H, m, H-6a and H-8), 1.90-2.00 (12H, s, 3H each, 4×OCOCH$_3$), 2.06-2.20 (2H, m, H-9 and H-6b), 3.00 (1H, m, H-5), 3.60 (3H, s, H-12), 3.70 (1H, m, H-5'), 4.09 (1H, m, H-6'b), 4.17 (1H, m, H-6'a), 4.82 (1H, m, H-1'), 4.97 (1H, d J=5.9 Hz, H-2'), 5.10 (2H, m, H-7 and H-1), 5.20 (2H, m, H-3' and H-4'), 5.25 (1H, d, J=9.5 Hz, H-2'''a), 5.70 (1H, m, H-1'''), 6.94 (1H, m, H-2'''b), 7.30 (1H, s, H-3), $^{13}$CNMR (CDCl$_3$): C-1 95.70d, C-3 149.40d, C-4 113.80s, C-5 30.60d, C-6 39.20t, C-7 77.00d, C-8 39.20d, C-9 46.40d, C-10 12.50q, C-11 164.00s, C-12 50.90q, C-1' 96.60d, C-2' 71.60d, C-3' 72.80d, C-4' 69.20d, C-5' 72.90d, C-6' 62.60t, C-1'' 170.00s, C-1''' 121.90d, C-2''' 147.00t, C-7-$\underline{C}$OCH$_3$ (165.5s), C-7-CO$\underline{CH}_3$ (20.0q), C-2'-$\underline{C}$OCH$_3$ (169.4s), C-2'-CO$\underline{CH}_3$ (20.6q), C-3'-$\underline{C}$OCH$_3$ (168.4s), C-3'-CO$\underline{CH}_3$ (20.2q), C-4'-$\underline{C}$OCH$_3$ (168.50s), C-4'-CO$\underline{CH}_3$ (20.3q), FABMS: m/z 626 [M$^+$], Elemental analysis for C$_{29}$H$_{38}$O$_{15}$ Calc. C, 55.59, H, 6.1; Observ; C, 55.2, H, 6.0; 12: Yield 81%, m.p. 148° C., $^1$H NMR (CDCl$_3$): 1.00 (3H, d, J=6.2 Hz, H-10), 1.69-1.87 (2H, m, H-6b and H-8), 1.92-2.06 (12H, s, 3H each, 4×OCOCH$_3$), 2.25 (2H, m, H-9 and H-6a), 3.00 (1H, m, H-5), 3.70 (3H, s, H-12), 3.90 (1H, m, H-5'), 4.30 (1H, m, H-6'b), 4.35 (1H, m, H-6'a), 4.90 (1H, d, J=7.6 Hz, H-1'), 5.10 (1H, t, J=9.0 Hz, H-2'), 5.20 (1H, brs, H-7), 5.30 (2H, m, H-1' and H-3'), 5.40 (1H, t, J=9.9 Hz, H-4'), 7.30 (1H, s, H-3), 7.70 (1H, t, J=7.2 Hz, H-5'''), 8.30 (1H, d, J=6.7 Hz, H-6'''), 8.40 (1H, d, J=8.0 Hz, H-4'''), 8.80 (1H, s, H-2'''), $^{13}$CNMR (CDCl$_3$): C-1 95.50d, C-3 149.30d, C-4 113.90s, C-5 30.50d, C-6 39.20t, C-7 77.00d, C-8 39.20d, C-9 46.30d, C-10 12.50q, C-11 163.40s, C-12 51.00q, C-1' 96.50d, C-2' 71.20d, C-3' 72.30d, C-4' 70.80d, C-5' 72.80d, C-6' 62.40t, C-1'', 170.30s, C-1''' 131.10s, C-2'''124.80d, C-3'''149.00s, C-4''' 127.90d, C-5''' 129.80d, C-6''' 135.10d, C-7-$\underline{C}$OCH$_3$ (167.0s), C-7-CO$\underline{CH}_3$ (20.0q), C-2'-$\underline{C}$OCH$_3$ (167.0s), C-2'-CO$\underline{CH}_3$ (20.0q), C-3'-$\underline{C}$OCH$_3$ (168.9s), C-3'-CO$\underline{CH}_3$ (20.3q), C-4'-$\underline{C}$OCH$_3$ (169.8s), C-4'-CO$\underline{CH}_3$ (20.4q), FABMS: m/z 707 [M$^+$], Elemental analysis for C$_{32}$H$_{37}$NO$_{17}$ Calc. C, 54.3, H, 5.2; Observ; C, 53.9, H, 5.1.

EXAMPLE-5

Cytotoxicity Testing of Loganin (1) and its Analogues 2-12

Cytotoxicity testing In-vitro was done by the method of Woerdenberg et al[17]. 2×10$^3$ cells/well were incubated in the 5% CO$_2$, 95% atmosphere and 37° C. in CO$_2$ incubator for 24 h to enable them to adhere properly to the 96 well polysterene microplate (Grenier, Germany). Test compounds dissolved in 100% DMSO (Merck, Germany) in at least five doses were added and left for four hour after which the compound plus media was replaced with fresh media and the cell were incubated for another 48 h in the CO$_2$ incubator at 37° C. The concentration of DMSO used in our experiment never exceeded 1 %, which was found to be non toxic to cells. Then, 10 µL from 5 mg/ml stock of MTT [3-(4,5-dimethylthiazol-2-yl)-2,5-diphenyltetrazolium bromide; Sigma M 2128] was added, and plate were incubated at 37° C. for 4 h. 100 µL of dimethylsulfoxide (DMSO, Merck, Germany) were added to all wells and mixed thoroughly to dissolve the dark blue crystal. After a few minute at room temperature to ensure that all crystal were dissolve, the plate were read on a Spectra Max 190 Microplate Elisa Reader (Molecular Devices Inc., U.S.A), at 570 nm. Plate were normally read within 1 h of adding the DMSO. The experiment was done in triplicate and the inhibitory concentration (IC) values were calculated as; % INHIBITION=[1−OD (570 nm) of sample well/OD (570 nm) of control well]×100. IC$_{50}$ is the concentration µg/mL required for 50% inhibition of cell growth as compared to that of untreated control.

EXAMPLE-6

Cytotoxic Activity of Loganin 1 and its Analogues 2-12

Loganin and its synthetic anlogues were evaluated in-vitro for their anticancer activity against human breast (MCF-7), Ovary (PA-1), Liver (WRL), Suspension Colon (COLO-320) and Adherent colon (CaCo2) cancer cell lines by MTT assay and results are given in Table-1. From the Tables 1 it is evident that the parent molecule loganin showed significant cytotoxic activity against all the tested human cancer cell lines. On comparing the cytotoxicity of loganin with its synthetic analogues, it is clear that protection of primary alcoholic group of sugar residue with trityl chloride and acetylation of secondary alcoholic group in aglycon and sugar residue of loganin resulted into analogues 2 and 3 having enhanced cytotoxic activity than the starting material loganin against all the tested human cancer cell lines. On the other hand deprotection of primary alcoholic group of sugar residue results the compound with abolished cytotoxicity but it is interesting to note that when the partially protected compound 4 is acylated/ arylated with different acid chlorides/acid anhydrides, drastic enhancement in cytotoxic activity for resulting analogues was observed. Careful observation revealed that when analogue 4 was arylated with benzoyl group having an electron donating substituents, showed significant enhancement in the cytotoxicity for the resulting analogue 11, while, the compound 4 when arylated with benzoyl group having electron withdrawing substituent such as analogue 12, it slightly decreased the activity in comparison to analogue 11. Similarly when compound 4 was acylated with hydrocarbons with small to moderate chain size (C$_3$-C$_{12}$), the activity also increased drastically for all the five tested human cancer cell lines in comparison to the starting material, loganin, but when the length of hydrocarbon increased (above $C_{12}$) the activity of resulting compounds decreased drastically. Interestingly introduction of a double bond in the aliphatic chain such as in case of analogue 9, totally abolished the activity. But it was interesting to note that introduction of a gem dimethyl group in the terminal carbon of the double bond in the above analogue 9, resulted in the significant enhancement of anticancer activity as depicted in analogue 10. It might be due to the enhancement in the bulkiness and/or lipophilicity of the molecule due to increase of two more methyl groups.

On comparing our results with the known anticancer drug, vinblastine it was observed that two semi synthetic analogues 6 and 11 showed 13 times higher activity against the human suspension colon (COLO-320) cancer cell lines while analogue 11 showed 8 times higher activity against human adherent colon cancer cell line (CaCO2) than those for vinblastine.

TABLE 1

Anticancer activity of loganin (1) and its derivatives 2-12 (μg/ml) by MTT assay against human cancer cell lines.

| Compounds | MCF-7 $IC_{50}$ | PA-1 $IC_{50}$ | WRL $IC_{50}$ | COLO-320 $IC_{50}$ | CaCo2 $IC_{50}$ | Dosage range $IC_{50}$ |
|---|---|---|---|---|---|---|
| 1 | 4.85 | 1.45 | 1.86 | 1.00 | 1.28 | 1.0-5.0 |
| 2 | 1.00 | 0.65 | 1.86 | 0.25 | 0.56 | 0.25-2.0 |
| 3 | 1.20 | 1.20 | 2.44 | 0.82 | 3.45 | 0.80-3.5 |
| 4 | IA | IA | IA | IA | IA | — |
| 5 | 1.88 | 1.24 | 2.65 | 0.85 | 2.85 | 0.80-3.0 |
| 6 | 0.24 | 0.15 | 0.85 | 0.04 | 0.42 | 0.04-0.85 |
| 7 | 24.60 | 6.5 | 58.50 | 30.00 | IA | 6.5-59.0 |
| 8 | IA | IA | IA | IA | IA | — |
| 9 | IA | IA | IA | IA | IA | — |
| 10 | 1.00 | 0.65 | 1.20 | 0.08 | 0.80 | 0.08-1.20 |
| 11 | 0.25 | 0.10 | 0.54 | 0.04 | 0.06 | 0.044-3.54 |
| 12 | 1.25 | 0.85 | 3.20 | 0.44 | 1.00 | 0.44-3.20 |
| Vinblastine | 0.02 | 0.025 | 1.45 | 0.52 | 0.46 | 0.02-1.45 |

IA = Inactive

We claim:

1. A loganin analogue of formula I

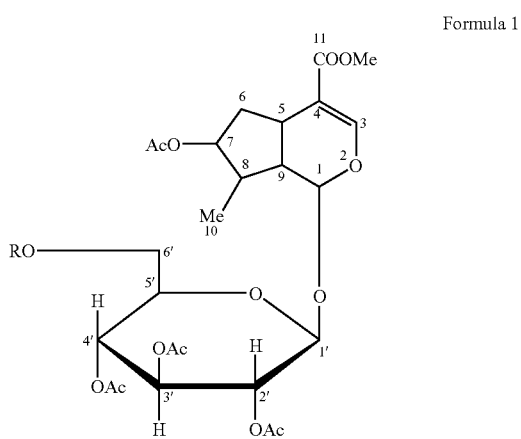

Formula 1 wherein R is

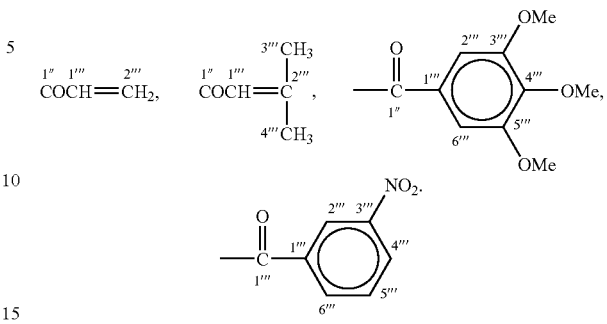

2. The loganin analogue of claim 1 selected from the group consisting of the following compounds:
    2',3',4',7-tetra-O-acetyl-6'-O-propionylloganin (5),
    2',3',4',7-tetra-O-acetyl-6'-O-lauroylloganin (6),
    2',3',4',7-tetra-O-acetyl-6'-O-myristoylloganin (7),
    2',3',4',7-tetra-O-acetyl-6'-O-palmitoylloganin (8),
    2',3',4',7-tetra-O-acetyl-6'-O-acryloylloganin (9),
    2',3',4',7-tetra-O-acetyl-6'-O-3''',3'''-dimethyl acryloylloganin (10),
    2',3',4',7-tetra-O-acetyl-6'-O-(3''',4''',5'''-trimethoxy) benzoylloganin (11), and
    2',3',4',7-tetra-O-acetyl-6'-O-3'''-nitrobenzoylloganin (12).

3. A process for the preparation of the loganin analogue of claim 1, comprises the steps of:
    a) dissolving loganin in pyridine and reacting it with trityl chloride, under stirring, at a temperature in the range of 30-40° C., adding crushed ice to the above said reaction mixture and extracting the resultant mixture with chloroform and further extracting the resultant extract with about 6% HCl, followed by washing with water and drying by a known method to obtain 6'-O-tritylloganin (2),
    b) acylating the above said compound (2) in pyridine with acetic anhydride to obtain the compound 2',3',4',7-tetra-O-acetyl-6'-O-tritylloganin (3),
    c) hydrolyzing the above said compound obtained (3) in step (b) by dissolving it in 70-90% acetic acid solution and refluxing it, at 70-90° C., for about 1 hour, adding water to above said reaction mixture, followed by extraction with chloroform, washing the resultant extract with water till it's neutralization, and drying by a known method to obtain the compound 2',3',4',7-tetra-O-acetylloganin (4),
    d) acylating the above said compound 2',3',4',7-tetra-O-acetylloganin (4) obtained in step (c) by dissolving it in either chloroform along with catalytic amount of 4-dimethylaminopyridine (DMAP) or in pyridine and reacting it with the desired acid chloride or acid anhydride, for an over night period, at a temperature of 30-45° C., adding ice to the above said reaction and extracting the resultant mixture with chloroform and further extracting the resultant chloroform extract with about 6% HCl, followed by washing with water until neutralization occurs, followed by purification and drying by known method to obtain the desired product from compounds (5) to (12).

4. The process of claim 3, wherein the amount of trityl chloride is in the range of 1-1.5 molar equivalents to loganin (1).

5. The process of claim 3, wherein the compounds (5) to (12) obtained are selected from the group consisting of:
2',3',4',7-tetra-O-acetyl-6'-O-propionylloganin (5), 2',3',4',7-tetra-O-acetyl-6'-O-lauroylloganin (6), 2',3',4',7-tetra-O-acetyl-6'-O-myristoylloganin (7), 2',3',4',7-tetra-O-6'-O-palmitoylloganin (8), 2',3',4',7-tetra-O-acety-6'-O-acryloyl loganin (9), 2',3',4',7-tetra-O-acetyl-6'-O-3''',3'''-dimethylacryloylloganin (10), 2',3',4',7-tetra-O-acetyl-6'-O-(3''',4''',5'''-trimethoxy) benzoyl loganin (11), and 2',3',4',7-tetra-O-acetyl-6'-O-3'''-nitrobenzoylloganin (12).

6. A pharmaceutical composition comprising a loganin analogue as defined in claim 1 or a pharmaceutically acceptable salt thereof in combination with a pharmaceutically acceptable carrier, adjuvant and/or additives.

7. The composition of claim 6, wherein the loganin analogue is selected from the group consisting of:
2',3',4',7-tetra-O-acetyl-6'-trityl loganin (3), 2',3',4',7-tetra-O-acetyl-6'-O-propionylloganin (5), 2',3',4',7-tetra-O-acetyl-6'-O-lauroylloganin (6), 2',3',4',7-tetra-O-acetyl-6'-O-myristoyl loganin (7), 2',3',4',7-tetra-O-acetyl-6'-O-palmitoyl loganin (8), 2',3',4',7-tetra-O-acetyl-6'-O-acrylolloganin (9), 2',3',4',7-tetra-O-acetyl-6'-O-3''',3'''-dimethylacryloylloganin (10), 2',3',4',7-tetra-O-acetyl-6'-O-trimethoxy (11), and 2',3',4',7-tetra-O-acetyl-6'-O-3'''-nitrobenzoylloganin (12).

8. The composition of claim 3, wherein the loganin is isolated from the fruit pulp of *Strychnos nux-vomica*.

9. The composition of claim 6 comprising wherein the dosage of 2',3',4',7-tetra-O-acetyl-6'-O-3''',4''',5'''-trimethoxybenzoylloganin (11) to be administered is selected to produce a concentration in vivo in the range of 0.04 to 0.54 micrograms/ml.

10. The composition of claim 6 comprising wherein the dosage of 2',3',4',7-tetra-O-acetyl-6'-O-3'''-nitrobenzoylloganin (12) to be administered is selected to produce a concentration in vivo in the range of 0.44 to 3.20 micrograms/ml.

11. The composition of claim 6 comprising wherein the dosage of 2',3',4',7-tetra-O-acetyl-6'-O-myristoylloganin (7) to be administered is selected to produce a concentration in vivo in the range of 6.5 to 59.0 micrograms/ml.

12. The composition of claim 6 comprising wherein the dosage of the loganin analogue to be administered is selected to produce a concentration in vivo in the range of 1 to 5 micrograms/ml.

13. The composition of claim 6 comprising wherein the dosage of 2',3',4',7-tetra-O-acetyl-6'-O-tritylloganin (3) to be administered is selected to produce a concentration in vivo in the range of 0.80 to 3.5 micrograms/ml.

14. The composition of claim 6 comprising wherein the dosage of 2',3',4',7-tetra-O-acetyl-6'-O-propionylloganin (5) to be administered is selected to produce a concentration in vivo in the range of 0.80 to 3.0 micrograms/ml.

15. The composition of claim 6 comprising wherein the dosage of 2',3',4',7-tetra-O-acetyl-6'-O-lauroylloganin (6) to be administered is selected to produce a concentration in vivo in the range of 0.04 to 0.85 micrograms/ml.

16. The composition of claim 6 comprising wherein the dosage of 2',3',4',7-tetra-O-acetyl-6'-O-3''',3'''-dimethylacryloylloganin (10) to be administered is selected to produce a concentration in vivo in the range of 0.8 to 1.2 micrograms/ml.

* * * * *